(12) United States Patent
Lynn

(10) Patent No.: US 10,737,054 B1
(45) Date of Patent: Aug. 11, 2020

(54) SOUND AND LIGHT CHAMBER

(71) Applicant: Gail Lynn, Westminster, CO (US)

(72) Inventor: Gail Lynn, Westminster, CO (US)

( * ) Notice: Subject to any disclaimer, the term of this patent is extended or adjusted under 35 U.S.C. 154(b) by 123 days.

(21) Appl. No.: 16/030,073

(22) Filed: Jul. 9, 2018

Related U.S. Application Data

(60) Provisional application No. 62/551,915, filed on Aug. 30, 2017.

(51) Int. Cl.
*A61M 21/00* (2006.01)
*A61M 21/02* (2006.01)

(52) U.S. Cl.
CPC ........ *A61M 21/0094* (2013.01); *A61M 21/02* (2013.01); *A61M 2021/0016* (2013.01); *A61M 2021/0027* (2013.01); *A61M 2021/0044* (2013.01)

(58) Field of Classification Search
CPC .............. A61M 21/02; A61M 21/0094; A61M 2021/0027; A61M 2205/59
USPC ........................................ 600/21, 22, 26–28
See application file for complete search history.

(56) References Cited

U.S. PATENT DOCUMENTS

| | | | | |
|---|---|---|---|---|
| 4,656,506 A | * | 4/1987 | Ritchey | G03B 21/00 348/39 |
| 5,427,433 A | * | 6/1995 | Holobaugh, Jr. | A47C 3/0255 248/370 |
| 6,544,165 B1 | * | 4/2003 | McNew | A61M 21/0094 600/27 |
| 9,188,850 B2 | * | 11/2015 | Turner | G03B 21/56 |
| 2005/0113723 A1 | * | 5/2005 | Ueyama | A61H 15/0078 601/15 |
| 2014/0316192 A1 | * | 10/2014 | de Zambotti | A61M 21/02 600/28 |
| 2016/0008568 A1 | * | 1/2016 | Attia | A61M 21/0094 600/28 |

OTHER PUBLICATIONS

Life Vessel Santa Barbara website available at http://lifevesselsb.com/what-is-the-life-vessel; copyright notice dated 2016.

* cited by examiner

*Primary Examiner* — Samuel G Gilbert
(74) *Attorney, Agent, or Firm* — John A. Arsenault; Daniel M. Dubuisson

(57) ABSTRACT

The system may include a chamber structure having a substantially oval or "egg" shaped outer shell. The system may also include an interior formed within the outer shell. A user area may be provided in the chamber structure substantially centered front to back and side to side within the outer shell. The system may also include at least one sound emitting device positioned to provide at least one person in the user area with a prescribed sound therapy. The system may also include at least one light emitting device selected to provide the person in the user area with a prescribed light therapy.

20 Claims, 5 Drawing Sheets

SOUND AND LIGHT CHAMBER

CROSS REFERENCE TO RELATED APPLICATIONS

This application claims the priority benefit of U.S. Provisional Patent Application No. 62/551,915 filed Aug. 30, 2017 titled "Harmonic Egg" of Gail Lynn, hereby incorporated by reference in its entirety as though fully set forth herein.

BACKGROUND

Many people's minds and bodies are afflicted by a variety of ailments, from diseases such as heart trouble and cancer, to mental illnesses, and stress and stress-induced ailments, to name only a few examples. In the past, these have often been treated with medication (e.g., pills or shots), along with various physical and/or mental therapies. More recently, homeopathic remedies have gained more widespread support as results have indicated successful treatments, and the general population has been educated on the undesired side effects of many traditional medicine. Other techniques to assist the body to heal naturally without the need for medication or invasive procedures are now also gaining in popularity and credibility.

DETAILED DESCRIPTION

Figure 1:
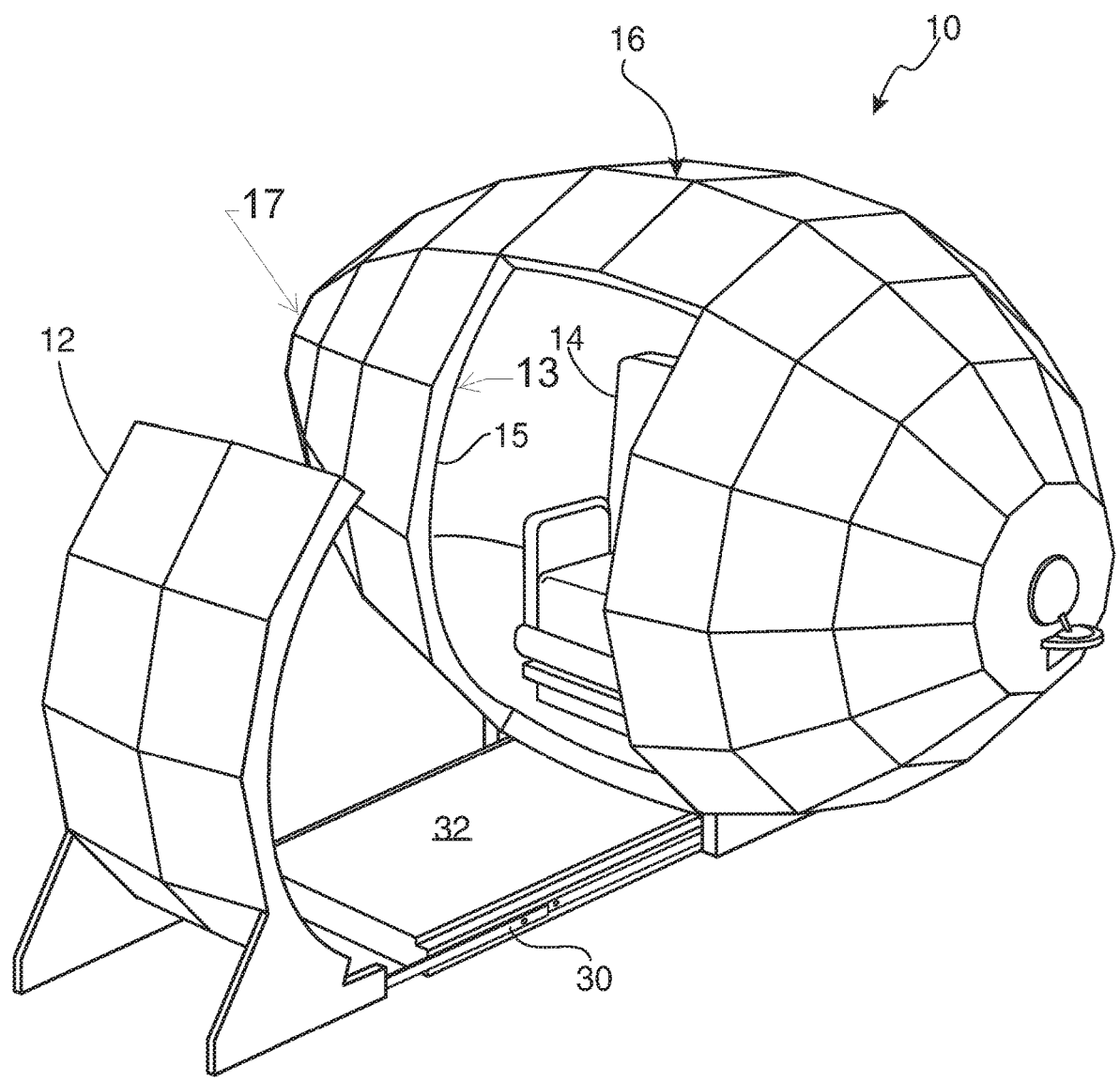
FIG. 1 is a perspective view of an example sound and light chamber, with an entrance door in an open position.

Technologies that use sound, vibrations, and light to heal are proving credible. The human body gets out of balance and needs a reset to remember how to heal naturally. The sound and light chamber disclosed herein can be implemented to successfully and non-invasively assist the human body to heal naturally. As such, the sound and light chamber disclosed herein may help to reduce a person's reliance on pills or other medications and/or invasive procedures (e.g., surgeries).

While the sound and light chamber disclosed herein is described primarily as an effective means for treating the human body, modifications thereto which will be well understood by those having ordinary skill in the art, may also be implemented to aid in the treatment of animals, such as domestic pets.

The sound and light chamber disclosed herein is based on the observed effects of several therapies on health and well-being. The sound and light chamber disclosed herein is the next generation healing chamber, based on observations of human persons before and after sessions, research on the modality, experts in the industry, and collaboration with the medical community.

In an example, the sound and light chamber disclosed herein is a large ellipse (e.g., substantially "egg" shaped). The person may be inside the chamber in a user area (e.g., a chair or otherwise). It is noted that other shapes are also contemplated. For example, the chamber may be configured to be more of an almond (e.g., Vesica Piscis) shape. In another example, the chamber may be vertical standing instead of the horizontal standing chamber shown in the drawings.

Before continuing, it is noted that as used herein, the terms "includes" and "including" mean, but is not limited to, "includes" or "including" and "includes at least" or "including at least." The term "based on" means "based on" and "based at least in part on."

Figure 2:
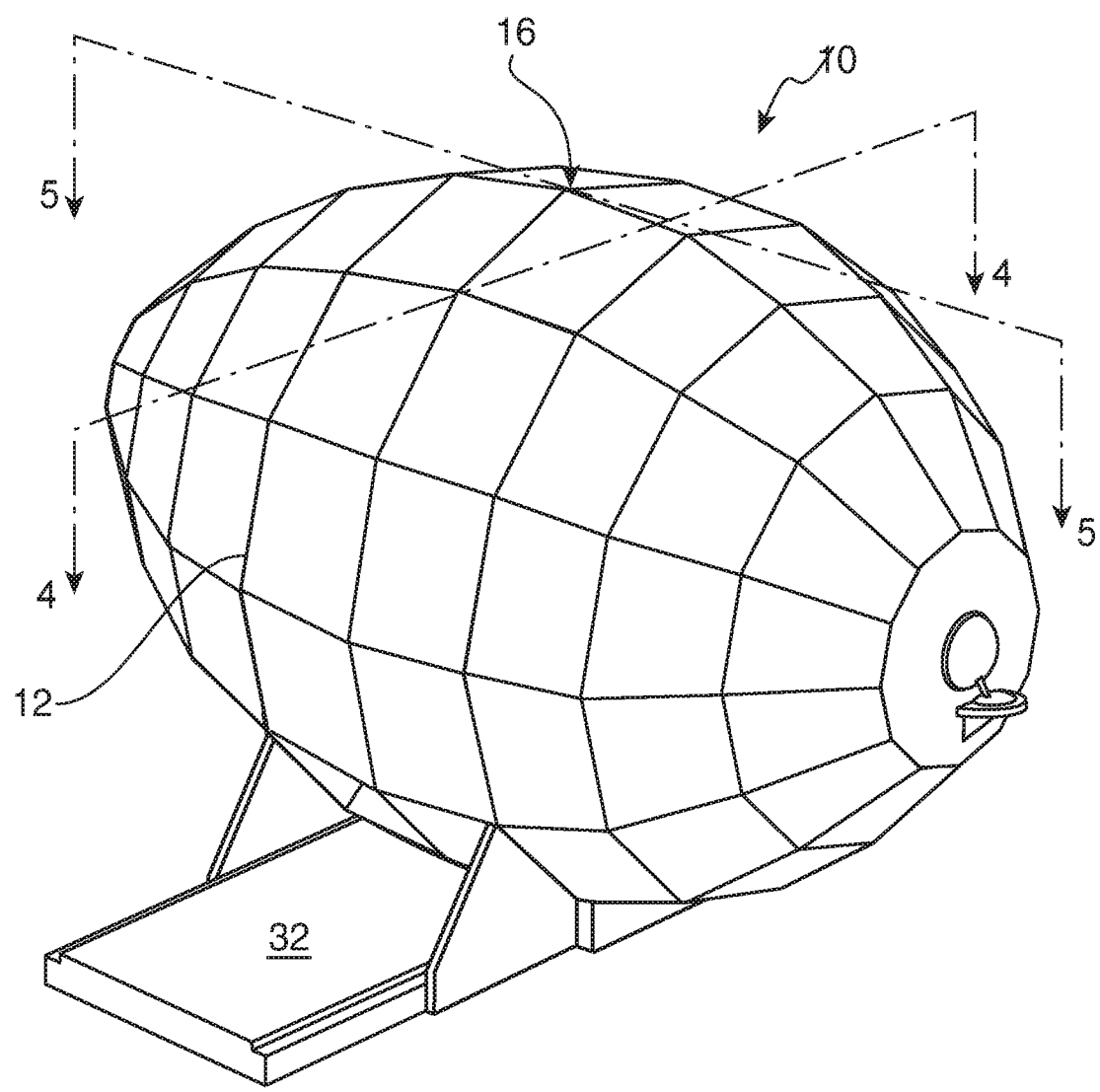
FIG. 2 is a perspective view of the example sound and light chamber shown in FIG. 1, with the entrance door in a closed position.

FIG. 1 is a perspective view of an example sound and light chamber 10, with an entrance door 12 in an open position. FIG. 2 is a perspective view of the example sound and light chamber 10 shown in FIG. 1, with the entrance door 12 in a closed position.

An example sound and light chamber system 10 includes a chamber structure 16. In an example, the chamber structure 16 may have an overall substantially oval or "egg" shaped shell having an exterior surface 15 that may be a combination of flat or substantially flat panels, and an interior surface or inner skin 13 that may be substantially smooth. The interior surface, exterior surface, and structure of the shell may collectively be referred to as a "shell" or "outer shell" 17. An interior area 19 may be formed within the shell or outer shell 17 of the chamber structure 16. In an example, the interior is curved and contoured generally in the shape of an egg. It is noted that other examples are also contemplated, and may include a smooth outside and/or inside, a paneled outside and/or inside, etc.

In an example, the door 12 is a sliding door. For example, the door 12 may slide on drawer slides 30 mounted to an entry platform 32 exterior to the chamber structure 16. The platform 32 may remain stationary, and the door slides along the length of the platform 32. When the door is closed, it forms a portion of the oval or egg shaped shell and interior. It is noted that other door configurations are also contemplated and the chamber 10 is not limited to any particular configuration or even number of doors. In other examples, the door may slide sideways, be hinged (e.g., on the top, bottom, or side), or otherwise configured to provide a cover for an opening into the chamber 10.

An example sound and light chamber system 10 also includes at least one sound emitting device 18a-18b. The sound emitting device 18a-18b may be positioned to provide a person 1 within the interior 19 of the shell 17 with a prescribed sound therapy. It is noted that generally the system 10 is intended for one person, or a baby or child sitting on a person's lap. However, in other examples, it may accommodate more than one person.

Although two sound emitting devices are shown in the drawings, one or more sound emitting device(s) may be provided. For example, a subwoofer may also be provided under the chair or seating area. Still other sound emitting devices may be provided. In addition, the sound emitting devices may be different types of sound emitting devices (e.g., different components of a sound system). Examples of selecting sound therapies are discussed in more detail below.

In an example, the sound emitting device 18a-18b is selected to produce little or no sound distortion. Examples are discussed in more detail below.

An example sound and light chamber system 10 also includes at least one light emitting device 20. The light emitting device(s) 20 may be selected to provide the person 1 within the interior 19 of the shell 17 with a prescribed light therapy. Although one light emitting device is shown in the drawings, one or more light emitting device(s) may be provided. In addition, the light emitting device(s) 20 may be different types of light emitting device(s). Examples of selecting light therapies are discussed in more detail below.

In an example, the light emitting device is selected to output a predetermined light frequency, spectrum, color, and/or duration of light. Examples are discussed in more detail below.

The example sound and light chamber system 10 may also include one or more aroma emitting device (not shown). The aroma emitting device may be selected to provide a prescribed aroma therapy.

Figure 3:
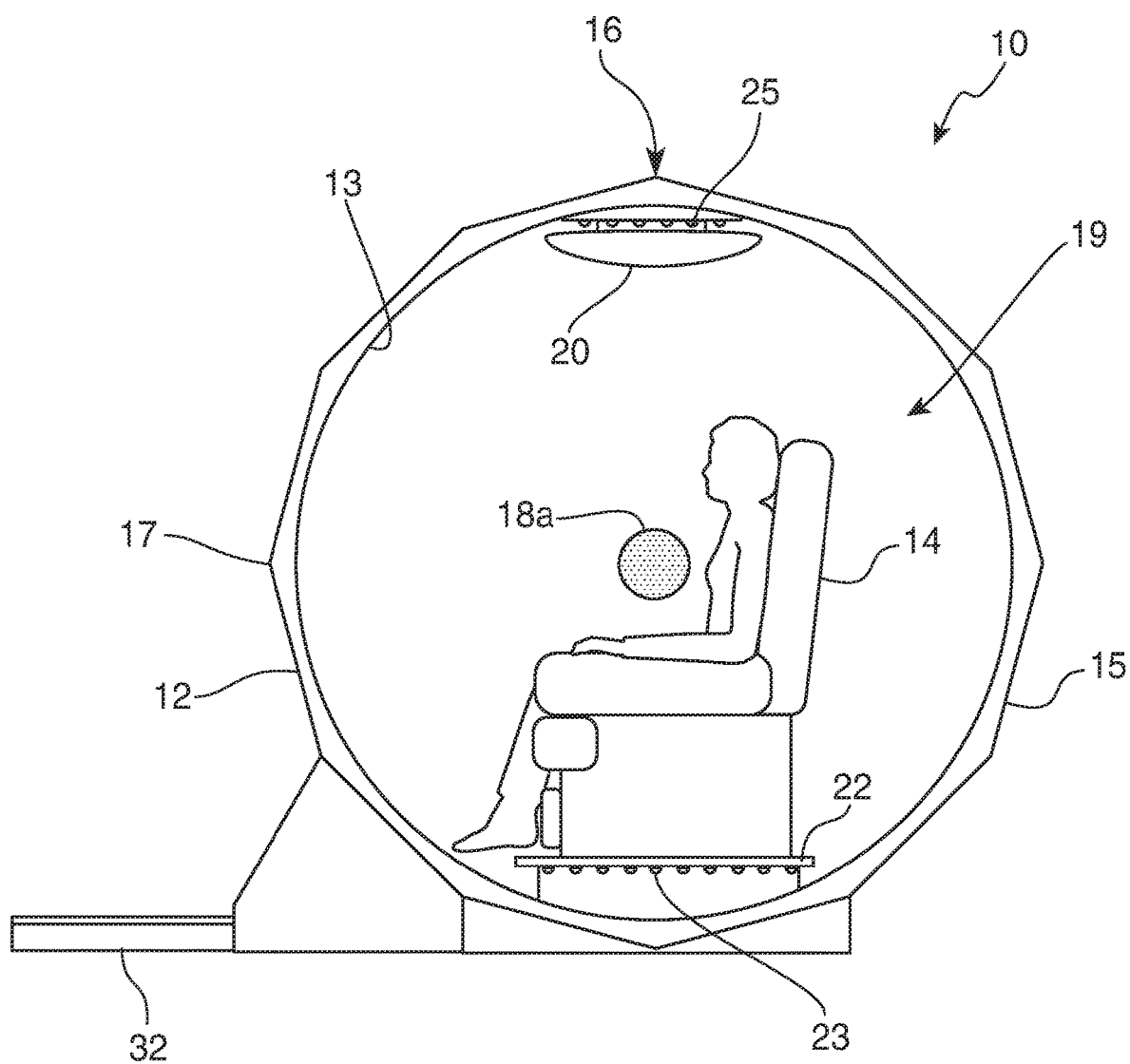
FIG. 3 is a side cross-sectional view of the example sound and light chamber taken along lines 4-4 in FIG. 2, showing a person in the chamber in a seated position.
Figure 4:
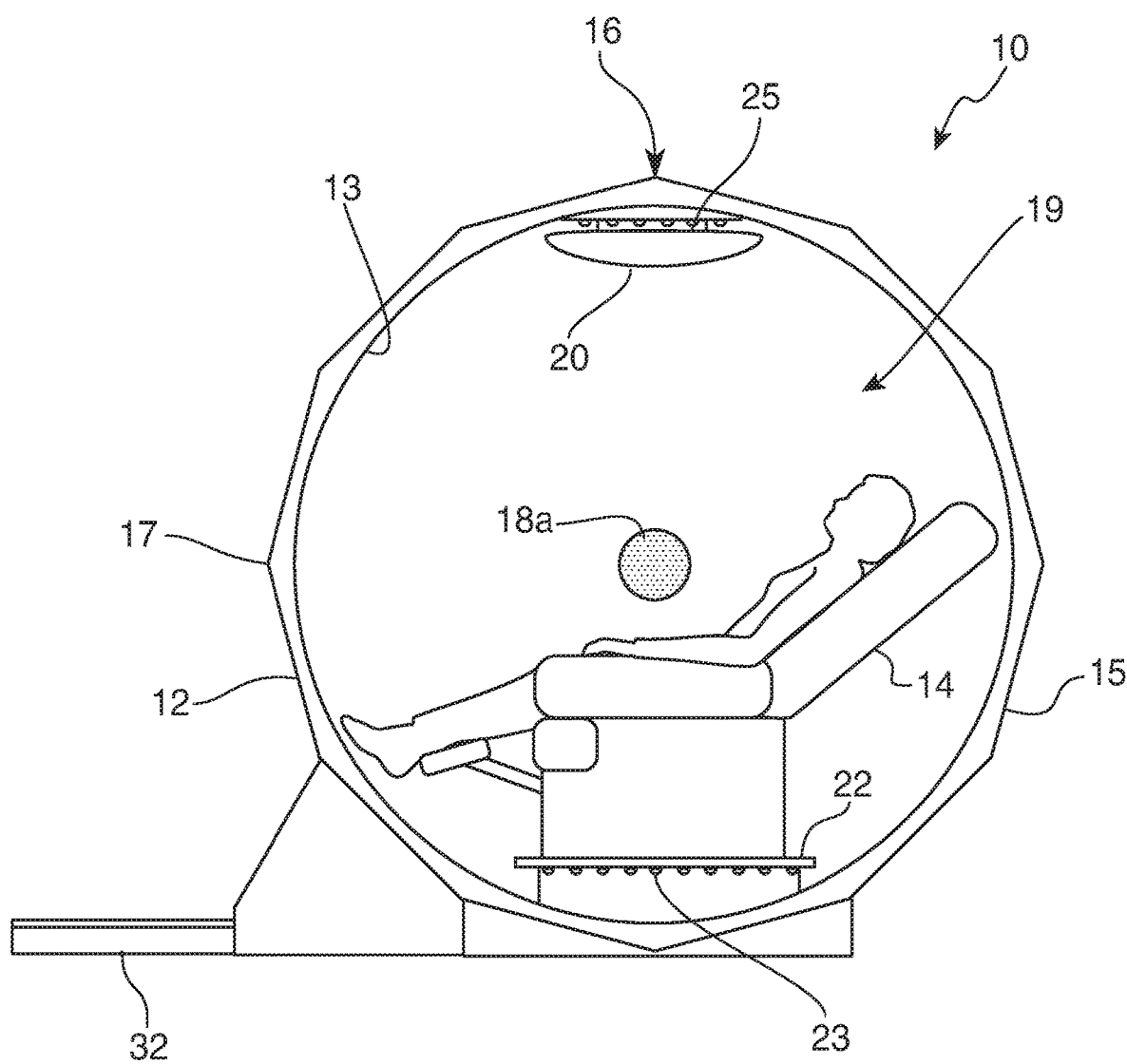
FIG. 4 is a side cross-sectional view of the example sound and light chamber taken along lines 4-4 in FIG. 2, showing a person in the chamber in a reclined position.
Figure 5:
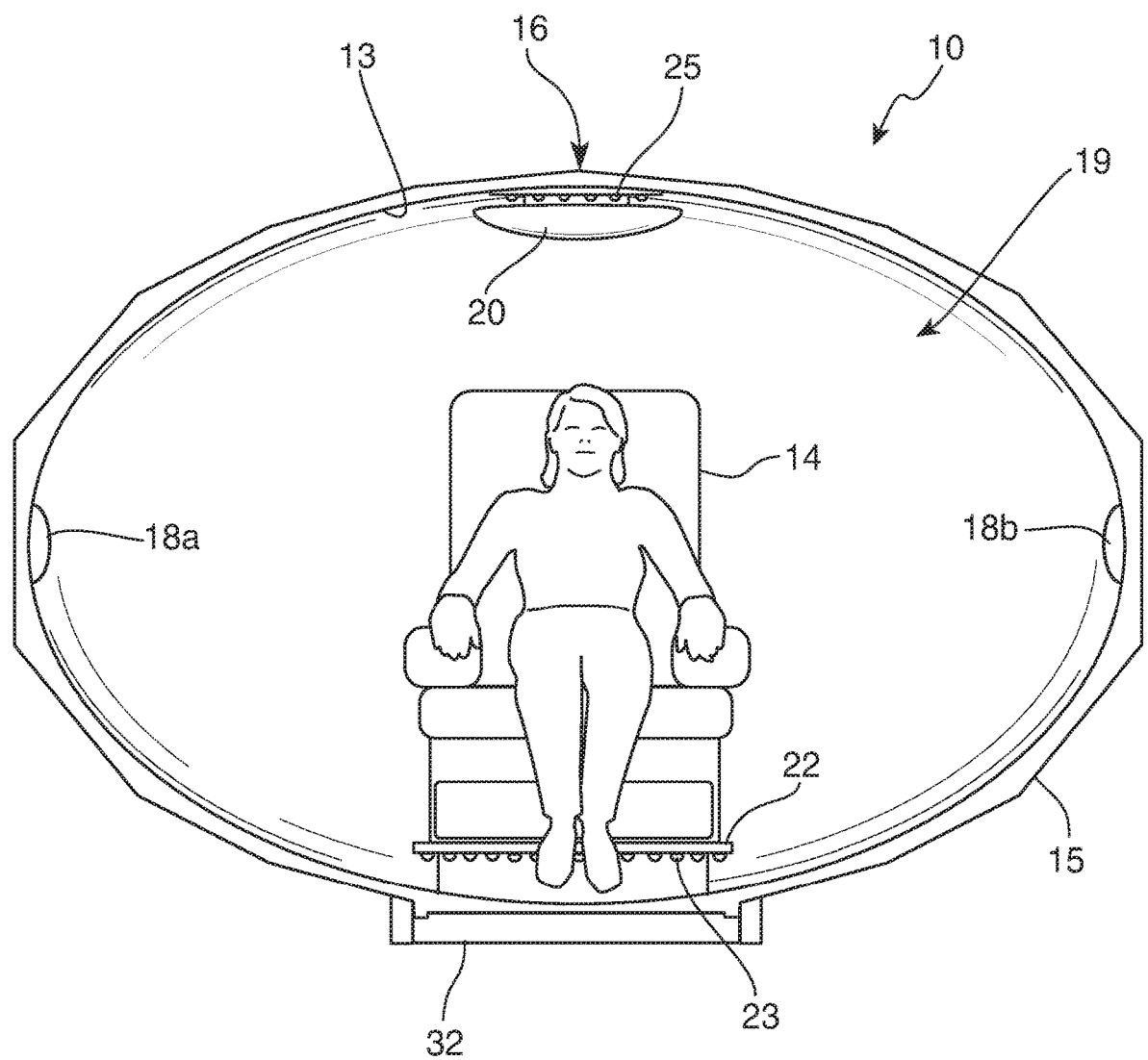
FIG. 5 is a cross-sectional view of the example sound and light chamber taken along lines 5-5 in FIG. 2, showing a person in the chamber in a seated position.

The example sound and light chamber system 10 may also include a chair 14 positioned on a floor or platform 22 of the chamber structure 16. In an example, the chair 14 is substantially centered front to back and side to side within the shell 17 of the chamber structure 16. In an example, the chair 14 is chair capable of shifting between an upright position, as seen in FIGS. 1 and 3, and a reclined position, as seen in FIGS. 4 and 5, or a variety of intermediate positions. Other examples are also contemplated, and may include but are not limited to, a chair facing another direction, a wheelchair or other removable chair, a bed or other platform to lay on, more than one chair or seating area for multiple simultaneous users, or no chair at all.

In an example, the chamber structure 16 is manufactured of natural materials. For example, the structure can be made of solid pine; and the skin/panels can be MDF, Masonite, birch, meranti or any type of material that will not crack or split in humid or dry conditions (e.g., hemp, cork or anything natural that will bend and hold the curve). It is noted that natural material/wood is preferred, as it generally does not hold energy or information and does not echo with the music. The material is bent into the shape of an ellipse to form a substantially "egg" shape of the chamber.

In an example, the interior of the chamber structure 16 is configured to resonate sound, e.g., in a holographic-like micro-environment. Instead of hearing the sound from a speaker, the person 1 hears sound in what is a "natural" broadcast. By natural, it is meant that the person 1 hears the sound above his or her head, even when there are not any speakers above the person's head.

In an example, the chamber structure 16 is sized so that it will fit in a typical 12'×12' room. However, the chamber structure 16 is not limited to any particular size, and may be made larger or smaller than this.

FIG. 3 is a side cross-sectional view of the example sound and light chamber 10 taken along lines 4-4 in FIG. 2, showing a person 1 in the chamber in a seated position in a chair 14. FIG. 4 is a side cross-sectional view of the example sound and light chamber 10 taken along lines 4-4 in FIG. 2, showing the person 1 in the chamber in the chair 14 in a reclined position. Also visible are the door 12, smooth interior surface 13, and exterior surface 15. FIG. 5 is a cross-sectional view of the example sound and light chamber 10 taken along lines 5-5 in FIG. 2, showing the person 1 in the chamber in the chair 14 in a seated position.

Lighting 23 and 25 is also shown, e.g., as the lights 23 may be mounted below the platform 22 and supplementing the lighting system 20. Every aspect of the example sound and light chamber 10 was considered for both the person and the operator or technician. These aspects include, but are not limited to the complexity of the technologies implemented, effectiveness of the therapies, ease of setup and operation, cost, music selections, and person comfort. Also visible are the smooth interior surface 13 and exterior surface 15.

In an example, the sound and light chamber 10 includes a chair 14. The chair 14 is provided for the person to sit in while they are in a session. The chair 14 also meets criteria for size and comfort for a wide variety of shapes and sizes of persons. Considerations include how the person feels sitting in the chair 14, and how the technician is able to comfortably and easily support the client. In the example shown in FIG. 4, the chair 14 is oriented with the footrest adjacent to and directed towards the door 12. The chair or the option may be modified, e.g., based on how the client will lie in the chamber (or possibly stand for the duration of the session. In another example, a platform may be provided to accommodate a wheelchair with a ramp for a person to roll into.

It is noted that lying flat for some persons is not comfortable or relaxing. Some persons have neck and back issues and want pillows and bolsters as props for comfort. In addition, some persons have a hard time rolling up from a flat position to exit the chamber. In an example, the chair 14 is a recliner that provides more positions for the person, and is more comfortable for persons. An example chair 14 reclines at a preferred angle which provides the person in a zero-gravity position where the feet are at the level of the heart or above the heart for the best results. It is noted that this angle will depend on the person size, weight, etc, and cannot be specified as a particular angle or range of angles.

In an example, the sound and light chamber 10 includes one or more sound emitting device (e.g., speakers 18a and 18b and subwoofer, not shown). While conventional speakers 18a and 18b are described herein which may be implemented output sound, other sound emitting devices may also be provided. In the example shown in FIGS. 3, 4 and 5, the speakers 18a, 18b are positioned at one or more lateral end portions of the interior 19 of the chamber structure 16 and directed towards the chair 14.

People's nervous systems tend to take distortion and make up "data" to fill in gaps to process information. The sound emitting device(s) are selected to reduce or altogether eliminate sound distortion and provide the purest sound.

In an example, the speakers, subwoofer, amplifier, and player for the music are selected from components that operate well together. For example, surround amplifiers and integrative amplifiers and subwoofers may be provided in the chamber 10. Speakers have different elements that make them relevant for different applications. However, other, higher quality speakers may also be provided. In addition, other shapes, sizes, and/or technology-type speakers may also be implemented for a high-quality therapeutic sound.

There is also the issue of the music and/or other sound(s) being played. Different instruments can physically effect and emotionally affect the body. When a CD or other source is compressed into an MP3 format, much of the quality, frequencies, musical and other information may be lost. Compression changes the original intent of how the music is to be enjoyed. MP3s are for convenience to fit 1,000 songs on an MP3 player.

The sound and light chamber 10 may implement higher quality "CD" resolution sound, giving the body and nervous system a purer listening experience. Higher than CD-quality sound may also be provided, e.g., as the industry changes and new technologies become available.

It is also important to select the right kind of music and the right tones and instruments and frequencies. These may be selected based at least in part on personal preference and the type of therapy. Aspects important to consider in sound selection include, but are not limited to: Who is the artist? What is their intention of the music? And other considerations.

Sound selection may be based at least in part on testing and identifying how different persons respond to the sound, paying attention to the sound quality and frequencies. These are important details that effect/affect the clients' response to therapy in the sound and light chamber 10.

The sound may also be selected to correspond with the light therapy. Different light frequencies are effective for healing the body and/or affective for healing the mind.

The lighting system 20 may provide options along all or part of the full color spectrum of lights. The lights and the right type of remote to control the lights and light settings. Lighting may include, but is not limited to, ultraviolet (UV) light, infrared (IR) light or other light sources. Other light technology now available or later developed enable the user to implement different lights and light frequencies based at least in part of the session, the person, and other considerations.

Session times may also be selected to be shorter or longer based on how the medical field treats a particular disease or other ailment. In an example protocol, a person stays in the chamber for 40 minutes with light and sound therapy, and then a powerful 10 minutes of silence in the chamber to integrate the session.

It has been shown that deep relaxing music helps persons heal and a period of silence helps integrate the healing. In another example, chiropractic care doctors are often trained to ensure the person rests at the office for a short time, to help the adjustment integrate and set into the body. Integration of all these modalities is important.

The sound and light chamber 10 may be implemented with single sessions and/or sets of sessions, e.g., depending on the condition of the person. For chronic conditions, sets of sessions hit the body more consistently with the energy to help the body heal faster. A person can choose to go slow or accelerate the healing process.

In an example, a single session takes about four (4) days to integrate before being able to schedule another session. A set of sessions may include a client coming every 4 days for approximately four to eight (4-8) sessions. That means a client may do a session, and then four (4) days later do another, and four (4) days later do another, for four to eight times total. After a set, a client can take a break from any and all other energy work for three to four weeks. After the break, the person can resume single or sets of sessions as desired.

In an example, the protocol for integrating sessions may also include dietary changes as well. This protocol may change to be more or less consecutive days or days in between sessions.

Although example protocols are described herein, it is noted that the protocols may change to have more of less integration time and different procedures based on the state of disease or other ailment being treated.

It is also noted that the examples described above are provided for purposes of illustration, and are not intended to be limiting. Other devices and/or device configurations may be utilized to carry out the operations described herein. The operations shown and described herein are provided to illustrate example implementations. The operations are not limited to the ordering shown. Still other operations may also be implemented.

By way of non-limiting illustration, the sound and/or music and lights may be adapted to newer technologies as those become available. Likewise, as medicine evolves and diseases evolve and change the sound and light chamber disclosed herein may be adapted to address those changes. For example, the procedures, music and/or sound selections, the shape of the sound technology, light technology and/or other modifications and/or additions may be implemented to enhance and/or accelerate healing.

Although described herein primarily as a light and sound chamber, other techniques, such as vibrations or motion may also be implemented as part of and/or in combination with the sound and light chamber disclosed herein. By way of illustration, aromatherapy may be provided in addition to, or instead of sound and/or light therapies.

The examples shown and described are provided for purposes of illustration and are not intended to be limiting. Still other examples are also contemplated.

The invention claimed is:

1. A sound and light chamber system, comprising:
   a chamber structure having a substantially oval or "egg" shaped outer shell;
   an interior formed within the outer shell;
   an entry platform exterior to the chamber structure;
   a door slidable along the entry platform, the door forming a portion of the oval or egg shaped outer shell when the door is closed;
   a user area positioned on a platform of the chamber structure substantially centered front to back and side to side within the outer shell;
   a chair for seating at least one person, wherein the chair is a reclining chair oriented with a backrest facing towards the door;
   at least one sound emitting device positioned at one or more lateral end portions of the interior of the chamber structure to provide the at least one person in the user area with a prescribed sound therapy; and
   at least one light emitting device selected to provide the at least one person in the user area with a prescribed light therapy.

2. A sound and light chamber system of claim 1, wherein the at least one sound emitting device is selected to produce little or no sound distortion for the person in the user area.

3. A sound and light chamber system of claim 1, wherein the at least one light emitting device is selected to output a predetermined light frequency and duration for the person in the user area.

4. A sound and light chamber system of claim 1, further comprising at least one aroma emitting device selected to provide the person in the user area with a prescribed aroma therapy.

5. A sound and light chamber system of claim 1, further comprising an interior skin that has a round cross section when viewed from the side, and an oval cross section when viewed from the front or back, and a plurality of flat panels forming an overall oval or egg shape exterior shell.

6. A sound and light chamber system, comprising:
   a chamber structure having a substantially oval or "egg" shaped outer shell, and an interior formed within the outer shell;
   an entry platform exterior to the chamber structure;
   at least one drawer slide mounted to the entry platform;
   a door slidable along the drawer slide(s), the door forming a portion of the oval or egg shaped outer shell when in a closed position;

a chair having a backrest and being capable of shifting between an upright position and a reclined position, wherein the chair is oriented with the backrest facing towards the door;

at least one sound emitting device positioned at one or more lateral end portions of the interior of the chamber structure to provide a person within the interior of the outer shell with a prescribed sound therapy; and at least one light emitting device selected to provide the person within the interior of the outer shell with a prescribed light therapy.

7. A sound and light chamber system of claim 6, wherein the at least one sound emitting device is selected to produce little or no sound distortion.

8. A sound and light chamber system of claim 6, wherein the at least one light emitting device is selected to output a predetermined light frequency and duration.

9. A sound and light chamber system of claim 6, further comprising at least one aroma emitting device selected to provide a prescribed aroma therapy.

10. A sound and light chamber system of claim 6, wherein the reclining chair is positioned on a platform of the chamber structure.

11. A sound and light chamber system of claim 10, wherein the reclining chair is substantially centered front to back and side to side within the outer shell and is directed towards the door.

12. A sound and light chamber system of claim 10, further comprising an interior surface that has a smooth round cross section when viewed from the side, and a smooth oval cross section when viewed from the front or rear, and a plurality of flat panels forming an overall oval or egg shape exterior shell.

13. A method for operating a sound and light chamber, comprising the steps of:

providing a chamber structure having a substantially oval shaped outer shell with an interior formed therein, an entry platform exterior to the chamber structure, a chair capable of shifting between an upright position and a reclined position and having a backrest facing towards a door, the door being slidable along the entry platform and forming a portion of the oval or egg shaped outer shell when the door is closed;

emitting sound from one or more sound emitting devices positioned at one or more lateral end portions of the interior of the outer shell according to a prescribed sound therapy; and emitting light for the person within the interior of the outer shell according to a prescribed light therapy.

14. The method for operating a sound and light chamber system of claim 13, wherein emitting the sound is with at least one sound emitting device selected to produce little or no sound distortion.

15. The method for operating a sound and light chamber system of claim 13, wherein emitting the light is with at least one light emitting device selected to output a predetermined light frequency and duration.

16. The method for operating a sound and light chamber system of claim 13, wherein emitting the light is for a predetermined duration according to a therapy protocol, and wherein emitting the sound is for a predetermined duration according to the therapy protocol.

17. The method for operating a sound and light chamber system of claim 13, further comprising emitting an aroma selected to provide a prescribed aroma therapy.

18. The method for operating a sound and light chamber system of claim 13, further comprising providing a reclining chair on a platform of the chamber structure.

19. The method for operating a sound and light chamber system of claim 18, wherein providing the reclining chair is substantially centered front to back and centered side to side within the outer shell.

20. The method for operating a sound and light chamber system of claim 18, further comprising:

providing an interior skin that has a round cross section when viewed from the side, and an oval cross section when viewed from the front or rear; and providing a plurality of flat panels forming an overall oval or egg shape exterior shell.

\* \* \* \* \*